United States Patent [19]

Haver

[11] Patent Number: Plant 6,594

[45] Date of Patent: Feb. 7, 1989

[54] MAPLE TREE NAMED MARELTOI

[76] Inventor: Herman H. Haver, 10411 N. 84th St., Omaha, Nebr. 68122

[21] Appl. No.: 2,792

[22] Filed: Jan. 12, 1987

[51] Int. Cl.[4] ..... A01H 5/00

[52] U.S. Cl. ..... Plt./51

[58] Field of Search ..... Plt./51

*Primary Examiner*—Robert E. Bagwill

*Attorney, Agent, or Firm*—Zarley, McKee, Thomte, Voorhees & Sease

[57] ABSTRACT

A Silver Maple tree named Mareltoi, having distinctively split, lacy leaves, and being slow growing, apparently seedless, and very cold-hardy.

4 Drawing Sheets

BACKGROUND OF THE INVENTION

The present invention relates to a new and distinctive variety of maple tree botanically known as *Acer saccharinum* which was originated by me in my nursery, located in Douglas County at 8032 Maple St., Omaha, Nebr. 68134.

At the beginning of my origination aforesaid, a small block of silver maple seedlings in my nursery had reached about seven feet in height when a storm damaged a few of them. I cut the damaged trees off about six inches about ground level. Later in the year, I noticed an unusual sport, or mutant growing from one of the trees that I had cut off. The sport had very slender lobes on the leaf, growing long, twisted and parallel to each other. The distance between leaves was very short which gave a very dense effect. I nursed the tree for six years, at which time it seeded. I planted the seeds and four out of every one hundred, on the average, had the characteristics of the mother tree. I nursed the seedlings of the different characteristics. I discovered that one of them was even more split, lacy and curled. It was also much slower growing and more dense than the mother tree. This tree is now ten years old, is thirteen feet tall and has never seeded and is much slower growing, only about one-third or less, than a silver maple.

BRIEF DESCRIPTION OF PHOTOGRAPHS

The accompanying photos show a typical specimen tree of my new variety, during both its green summer foliage and yellow autumn foliage states, as well as a close-up view of a typical leaf, depicting the growth habit and lacy leaf of a ten year old tree.

SUMMARY OF NEW VARIETY

My tree has a very split, lacy leaf with long, almost parallel, lobes that tend to twist. The growth of my tree is almost as slow as that of the *Acer ginnola,* or Amur Maple. My tree is ideal for the arid conditions of the midwest and plains states where it is difficult to grow the more dwarfed hard maple varieties. My tree responds well to bonsai, topiary or potted patio tree planting. It is apparently seedless.

DETAILED DESCRIPTION OF NEW VARIETY

In view of the foregoing, among other reasons, I am convinced that my new split leaf maple is a new and distinct variety, as particularly evidenced by the following unique combination of principal characteristics which are outstanding in the same and which distinguish it from all other varieties of which I am aware:

(1) A much slower growing habit as compared to all other silver maples.

(2) A more split, lacy leaf than any silver maple.

(3) Appears to be seedless.

(4) Corkscrew type twist to the leaf lobes.

(5) Gold petiole, midrib and veins.

(6) Good resistance to insects and blight.

I have asexually reproduced my tree by stem graft, cleft graft, saddle graft, bud graft and by rooting soft wood cuttings. In all tests, the asexually reproduced trees maintained their unusual characteristics, but all except the rooted cuttings were not as strong in roots, or as deep rooted. I have since reproduced only by rooting soft wood cuttings.

The following is a detailed description of my new variety of maple tree with color terminology in accordance with P.M.S. (Pantone Matching System).

Propagation: Holds its distinguishing characteristics through succeeding propagations by rooting soft-wood cuttings.

Tree: Very hardy. Not substantially different in form from average silver maple with great exception to being much smaller and slower growing.

Trunk: Smooth, brown. 469U.

Branches: Smooth with caraway seed type lenticels.

*Color.*—Brown 462C.

*Lenticels.*—Long, slender and very abundant — White.

Leaves: Medium thickness tissue. Overly abundant leaves.

*Color.*—Summer Green 349U with the Yellow 100U following out of the mid rib and veins into the leaf tissue.

*Underside.*—Silver.

*Midrib and veins.*—Yellow 100U.

*Petiole.*—Yellow 394U to partly Orangish Yellow 142U.

*Fall color.*—Yellow 394U to partly Orangish yellow 142U.

*Shape.*—Palmate but long, narrow major lobes running almost parallel to each other and having a cork screw twist to them.

*Size.*—Length of blade — 5 to 15 cm. Width of blade — 2½ to 5 cm. Length of petiole — 3 to 8 cm.

Flower buds: None.

Flowers: None.

Fruit: None.

Insect resistance: Less prone to aphid and cottony maple scale than common silver maple grown in same field.

General observations: While my new variety of silver maple resembles the species *Acer saccharinum,* Lactiniatum or Wieri in some respects, it is distinctly and strikingly different therefrom, particularly in respect to much more split and corkscrew, curled leaves with lobes running more parallel to each other. The leaves are more abundant and closer together as appearing to be seedless. The growth habit is about one-third of that of any other silver maple. My tree's slow growth and winter hardiness makes it a welcome addition to the midwest and plains states, to be used in place of dwarf split leaf hard maples that winter kill so easily. It is very controllable as a Bonzai, Topiary or potted patio tree.

I claim:

1. A new and distinct variewty of maple tree of the species botanically known as *Acer saccharinum,* substantially as herein shown and described, characterized particularly as to novelty by the unique combination of slow growth, harder wood, split lacy leaf, appearing seedless, very hardy, and resistant to blight and insects.

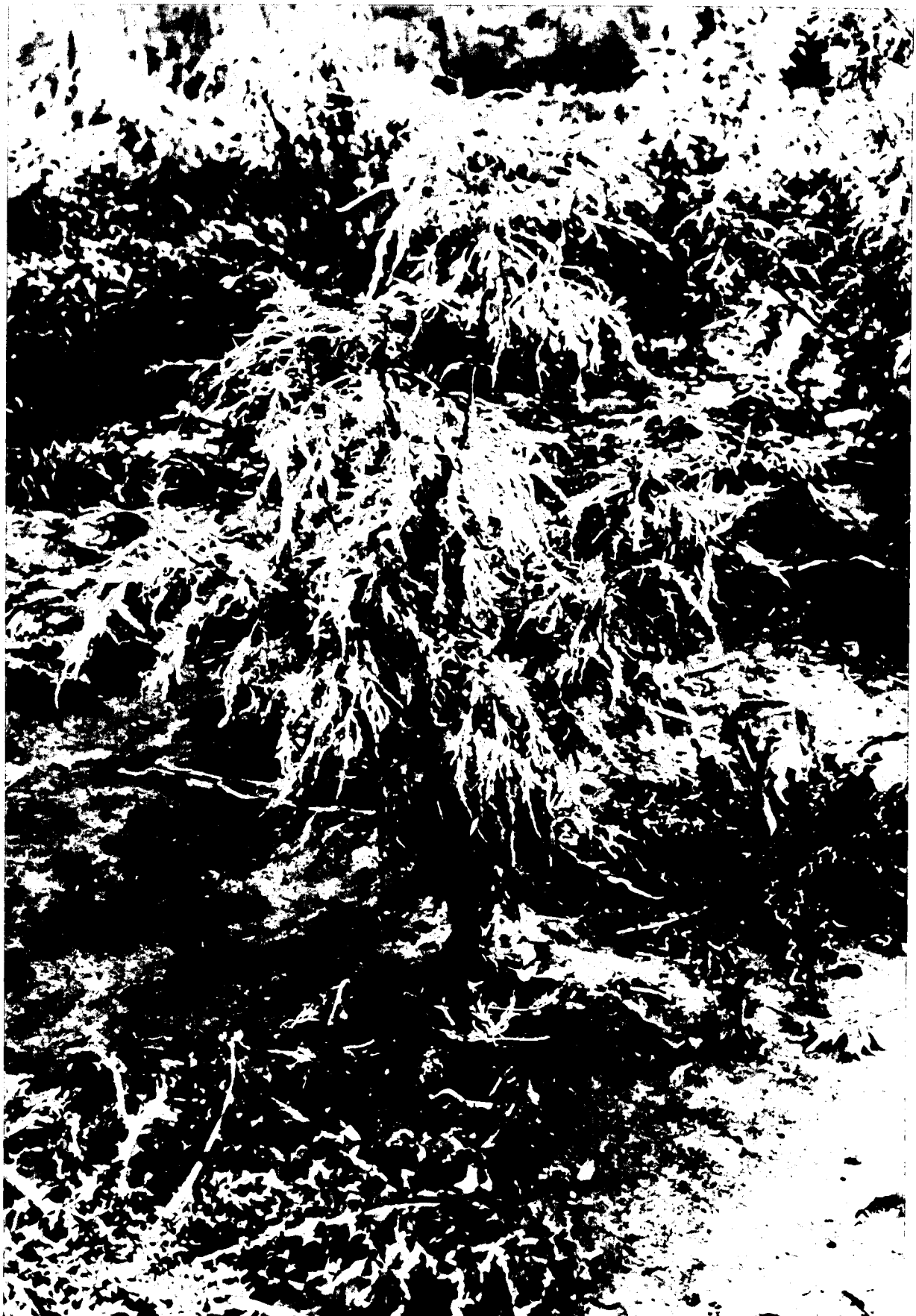

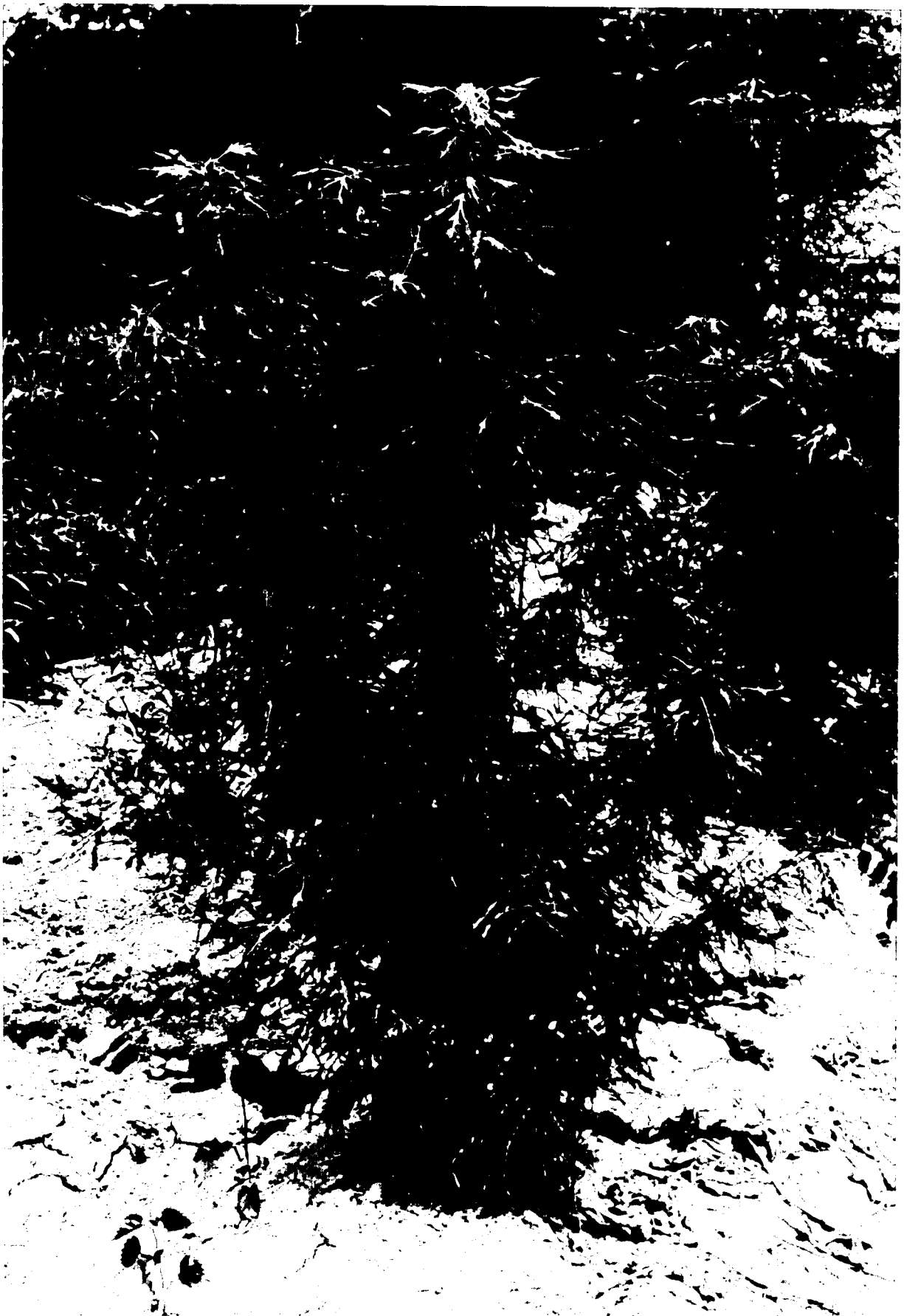

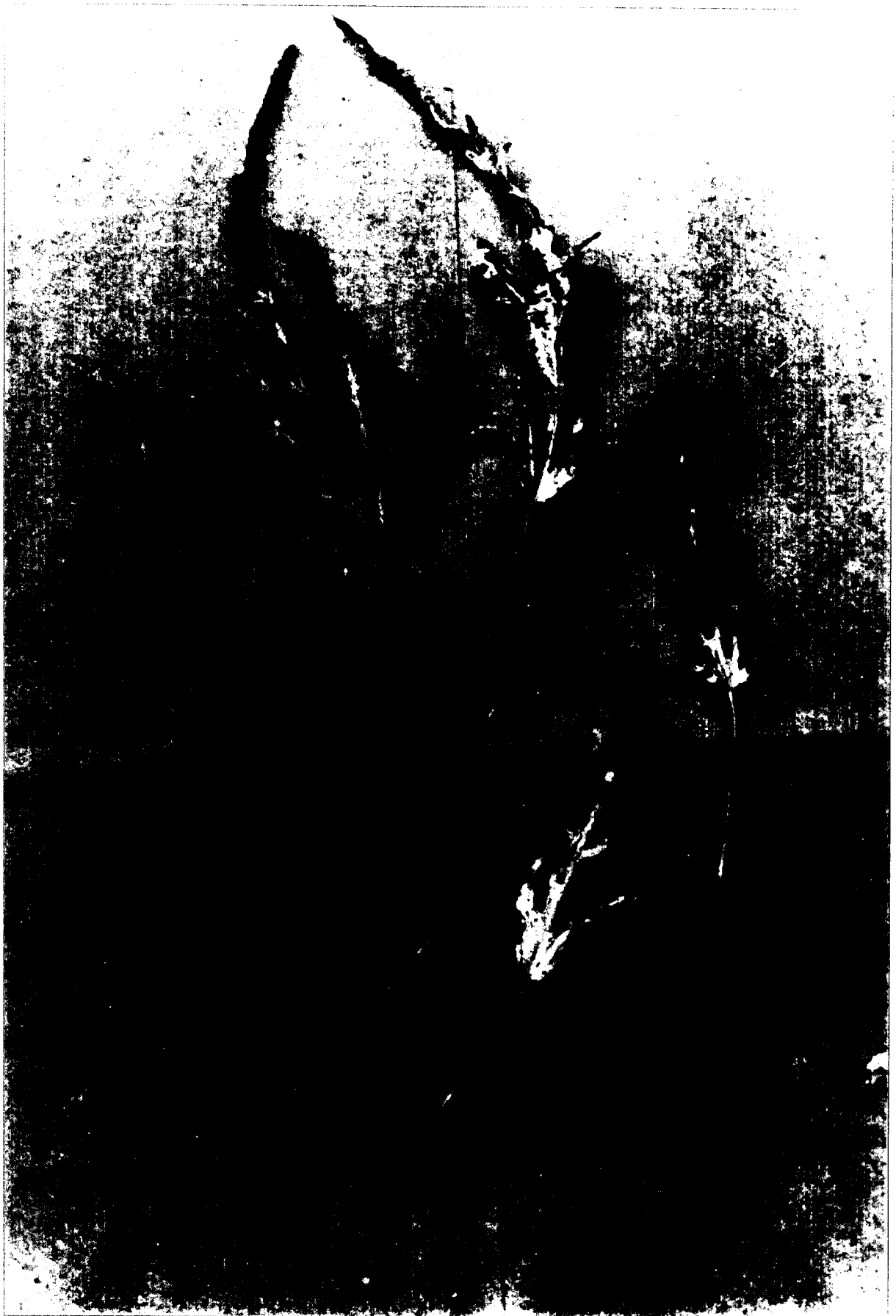

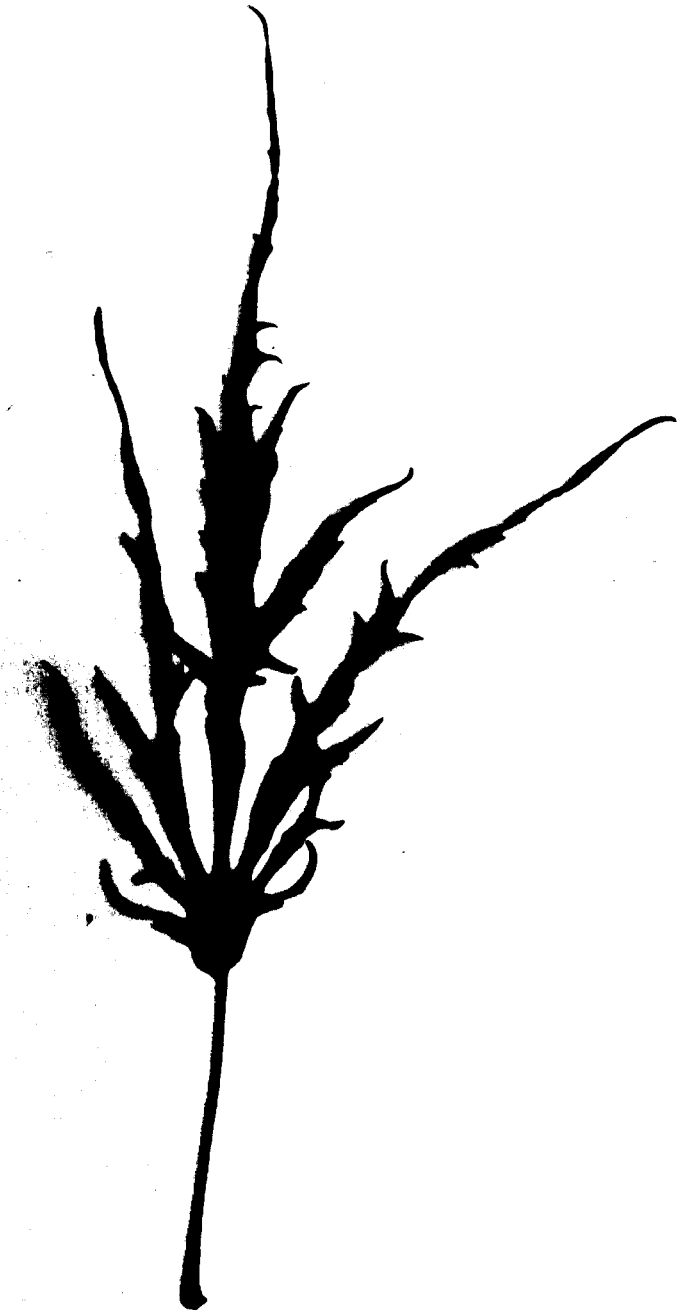

* * * * *